(12) United States Patent
Morita et al.

(10) Patent No.: US 12,349,865 B2
(45) Date of Patent: Jul. 8, 2025

(54) ENDOSCOPE HOOD

(71) Applicant: SEED CO., LTD., Tokyo (JP)

(72) Inventors: Yoshinori Morita, Kobe (JP);
Toshihiro Takamatsu, Kobe (JP);
Akitoshi Okino, Meguro-ku (JP);
Hidekazu Miyahara, Meguro-ku (JP);
Hiroaki Kawano, Meguro-ku (JP);
Haruka Ito, Bunkyo-ku (JP); Shiori Kaneda, Bunkyo-ku (JP); Toru Matsunaga, Bunkyo-ku (JP); Takao Sato, Bunkyo-ku (JP)

(73) Assignee: SEED CO., LTD., Tokyo (JP)

( * ) Notice: Subject to any disclaimer, the term of this patent is extended or adjusted under 35 U.S.C. 154(b) by 571 days.

(21) Appl. No.: 16/635,641

(22) PCT Filed: Jun. 25, 2018

(86) PCT No.: PCT/JP2018/023998
§ 371 (c)(1),
(2) Date: Jan. 31, 2020

(87) PCT Pub. No.: WO2019/026473
PCT Pub. Date: Feb. 7, 2019

(65) Prior Publication Data
US 2021/0127952 A1 May 6, 2021

(30) Foreign Application Priority Data

Aug. 1, 2017 (JP) .................................. 2017-149219

(51) Int. Cl.
*A61B 1/00* (2006.01)
*A61B 1/12* (2006.01)

(52) U.S. Cl.
CPC .......... *A61B 1/00089* (2013.01); *A61B 1/127* (2013.01)

(58) Field of Classification Search
CPC . A61B 1/00089; A61B 1/00101; A61B 1/126; A61B 1/00096; A61B 1/00137;
(Continued)

(56) References Cited

U.S. PATENT DOCUMENTS 4,943,618 A * 7/1990 Stoy .......................... C08F 8/00
525/367
5,252,392 A * 10/1993 Goto ...................... G11B 5/716
428/425.9
(Continued)

FOREIGN PATENT DOCUMENTS

EP 0 595 226 A2 5/1994
EP 1 759 627 A1 3/2007
(Continued)

OTHER PUBLICATIONS

International Search Report issued in corresponding International Application No. PCT/JP2018/023998 dated Sep. 25, 2018, with English translation.
(Continued)

*Primary Examiner* — Ryan N Henderson
*Assistant Examiner* — Pamela F Wu
(74) *Attorney, Agent, or Firm* — Troutman Pepper Locke LLP (57) ABSTRACT

An endoscope hood having excellent antifogging properties and antifouling properties. The endoscope hood is configured to be mounted on an insertion side end of an endoscope. The endoscope hood comprises a cylindrical exterior portion and a disc portion provided in contact with an inner surface of the exterior portion. The exterior portion and the disc portion are formed integrally or separately. At least the disc portion is made of a hydrogel.

4 Claims, 8 Drawing Sheets

(58) Field of Classification Search
CPC ............ A61B 1/00135; A61B 1/00131; A61B 1/0008; G02B 23/2476
See application file for complete search history.

(56) References Cited

U.S. PATENT DOCUMENTS

| | | | |
|---|---|---|---|
| 5,443,781 A * | 8/1995 | Saab ................... | A61B 1/0011 264/320 |
| 6,428,839 B1 * | 8/2002 | Kunzler ................ | C08J 7/0427 427/430.1 |
| 6,530,881 B1 * | 3/2003 | Ailinger ................ | B29C 55/22 600/114 |
| 2001/0053909 A1 * | 12/2001 | Nakada ............... | A61B 1/00089 606/46 |
| 2004/0114105 A1 * | 6/2004 | Shimoyama ............ | C08J 7/048 351/159.78 |
| 2005/0147685 A1 * | 7/2005 | Osada ................ | C08F 220/585 604/372 |
| 2006/0069312 A1 * | 3/2006 | O'Connor ............. | A61B 1/253 600/176 |
| 2006/0136064 A1 * | 6/2006 | Sherman ............... | A61L 27/446 623/17.16 |
| 2006/0258908 A1 | 11/2006 | Stenanchki et al. | |
| 2008/0228035 A1 | 9/2008 | Hagihara et al. | |
| 2009/0196845 A1 * | 8/2009 | Xia ......................... | C11D 3/48 514/642 |
| 2009/0247831 A1 | 10/2009 | Miyamoto et al. | |
| 2011/0189420 A1 * | 8/2011 | Masuda .................... | C08F 2/44 264/129 |
| 2011/0237766 A1 * | 9/2011 | Maggio ................ | C09D 133/24 556/419 |
| 2012/0026457 A1 | 2/2012 | Qiu et al. | |
| 2012/0109272 A1 * | 5/2012 | Knoll ................ | A61N 1/37518 607/116 |
| 2012/0209074 A1 | 8/2012 | Titus | |
| 2012/0283381 A1 * | 11/2012 | Tamiya ................... | C08L 83/10 524/588 |
| 2012/0318772 A1 * | 12/2012 | Minoura ................ | C25D 11/04 216/52 |
| 2013/0046138 A1 * | 2/2013 | McLawhorn ...... | A61B 1/00087 600/104 |
| 2013/0090527 A1 * | 4/2013 | Axon .................... | A61M 25/04 600/114 |
| 2015/0133566 A1 * | 5/2015 | Gong .................... | C09D 143/02 524/813 |
| 2017/0066207 A1 * | 3/2017 | Hayashi .............. | C08F 290/067 |
| 2017/0204213 A1 * | 7/2017 | Kato ........................ | A61L 27/52 |
| 2018/0037690 A1 * | 2/2018 | Aitken ................ | C08F 283/124 |
| 2019/0016900 A1 * | 1/2019 | Hayashi .................. | C09D 7/65 |
| 2019/0099511 A1 * | 4/2019 | Yamashita ........... | C09D 133/24 |
| 2020/0281448 A1 * | 9/2020 | Titus ....................... | A61B 1/07 |

FOREIGN PATENT DOCUMENTS

| | | | |
|---|---|---|---|
| JP | 6-306250 | A | 11/1994 |
| JP | 11-047081 | A | 2/1999 |
| JP | 2004-267583 | A | 9/2004 |
| JP | 2007-20759 | A | 2/2007 |
| JP | 2007-151685 | A | 6/2007 |
| JP | 2009-213631 | A | 9/2009 |
| JP | 2009-240596 | A | 10/2009 |
| JP | 2014-510577 | A | 5/2014 |
| JP | 2014200974 | * | 10/2014 |
| JP | 2014-212835 | A | 11/2014 |
| JP | 3204800 | U | 5/2015 |
| JP | 2016-55103 | A | 4/2016 |
| WO | 2012/112755 | A2 | 8/2012 |

OTHER PUBLICATIONS

Supplementary European Search Report issued in corresponding European Patent Application No. 18 84 1503 dated Mar. 16, 2021.
Chilean Office Action issued in corresponding Chilean Patent Application No. 257-2020 dated Nov. 23, 2020, submitted with Chilean Attorney comments dated Dec. 17, 2020.

* cited by examiner

FIG. 4A
Before processing

FIG. 4B
After application or lard

FIG. 4C
After cleaning with water

FIG. 5A — Before processing

FIG. 5B — After application or lard

FIG. 5C — After cleaning with water

FIG. 6C After cleaning with water

FIG. 6B After application of lard

FIG. 6A Before processing

FIG. 7A Before processing

FIG. 7B After application of lard

FIG. 7C After cleaning with water

ENDOSCOPE HOOD

CROSS-REFERENCE TO RELATED APPLICATION

This is a U.S. National Phase Application under 35 U.S.C. § 371 of International Patent Application No. PCT/JP2018/023998, filed on Jun. 25, 2018, which claims priority of Japanese Patent Application No. 2017-149219, filed Aug. 1, 2017. The entire contents of which are hereby incorporated by reference.

FIELD OF THE INVENTION

The present invention relates to an endoscope hood to be attached to an insertion side end of an endoscope.

BACKGROUND

In an endoscope, a plurality of through-holes is formed in a longitudinal direction, and camera lenses or illumination lenses for securing visibility are arranged in these through-holes.

In the surgery or examination using the endoscope, a transparent hood is attached to a tip end of the endoscope so as to check the optimal distance from the tip end (insertion side end) of the endoscope to the living tissue and secure the visual field. Here, such a hood is made of acrylonitrile butadiene styrene (ABS), polycarbonate, vinyl chloride, or the like. In recent years, the hood has been made of a silicone rubber or the like so as to prevent damage to living tissues.

However, since such a hood is attached so as to check the optimal distance from the tip end of the endoscope to the living tissue and secure the visual field, and the part of the camera lens or the illumination lens is not covered, body fluid or fat and oil adhere and visibility became unclear in the examination or surgery using the endoscope mounted with the hood.

For the purpose of contamination resistance of the camera lens or the illumination lens, the above-described lens part also forms a coatable hood, and a hood subjected to antifogging treatment (JP H11-047081 A and JP 2004-267583 A), a hood provided with a hydrophilic coating (see JP 2007-151685 A and JP 2009-213631 A), and the like are disclosed. Furthermore, a technique of providing a liquid spraying mechanism to an endoscope and cleaning a lens part (see JP 2009-240596 A) is also disclosed.

SUMMARY

However, since the endoscope hood or the lens is made of a material having high lipophilicity, there is a problem that the affinity with body fluid or fat and oil is extremely high and it is impossible to completely remove attached body fluid or fat and oil.

Here, it cannot be said that the antifogging antifouling techniques disclosed in JP H11-047081 A, JP 2004-267583 A, JP 2007-151685 A, JP 2009-213631 A and JP 2009-240596 A have sufficient effects with respect to such problems. When haze or contamination in the endoscope hood or the lens is remarkable, the surgery or examination is interrupted, the endoscope is pulled out, the contamination is removed, and the endoscope is inserted again. Therefore, there has been a problem that the burden on patients is increased by prolonging the operation time or reinsertion.

Therefore, it is desirable to provide an endoscope hood which is excellent in antifogging properties and antifouling properties.

A first feature is an endoscope hood to be attached to an insertion side end of an endoscope, the endoscope hood including: a substantially cylindrical exterior portion; and a disc portion in circumferential contact with an inner surface of the endoscope, wherein the exterior portion and the disc portion are formed integrally and are made of a hydrogel.

A second feature is an endoscope hood to be attached to an insertion side end of an endoscope, the endoscope hood including: a substantially cylindrical exterior portion; and a disc portion in circumferential contact with an inner surface of the endoscope, wherein the exterior portion and the disc portion are respectively formed separately and are made of a hydrogel.

DETAILED DESCRIPTION

Hereinafter, embodiments will be described with reference to the drawings as appropriate. However, more detailed description than necessary may be omitted. For example, detailed description of already well-known matters or redundant description of substantially the same configuration may be omitted. This is for avoiding the unnecessary redundancy of the following description and facilitating the understanding of those skilled in the art.

The inventor provides the accompanying drawings and the following description so that those skilled in the art can sufficiently understand the present disclosure, and they are not intended to limit the claimed subject matter.

Figure 1A:
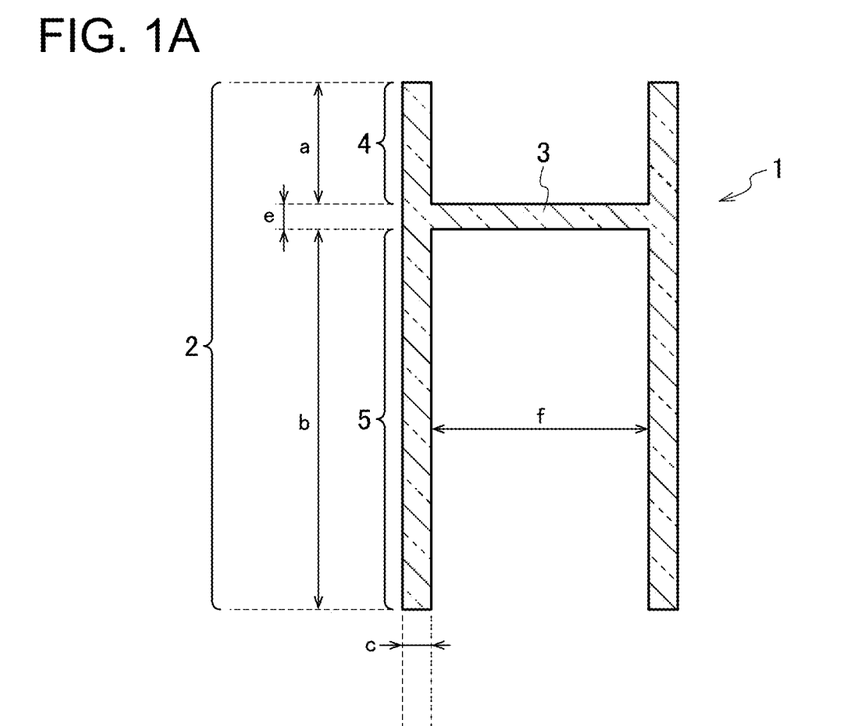
FIG. 1A is an example of a cross-sectional view and FIG. 1B is a plan view of an endoscope hood 1 according to a first embodiment.

Hereinafter, an endoscope hood 1 according to an embodiment will be described with reference to FIGS. 1A and 1B and 2. FIG. 1A is a diagram illustrating an example of a cross-sectional view of the endoscope hood 1 according to the present embodiment, FIG. 1B is a diagram illustrating an example of a plan view of the endoscope hood 1 according to the present embodiment, and FIG. 2 is a diagram illustrating an example of a state in which the endoscope hood 1 according to the present embodiment is attached to an endoscope 100.

Figure 1B:
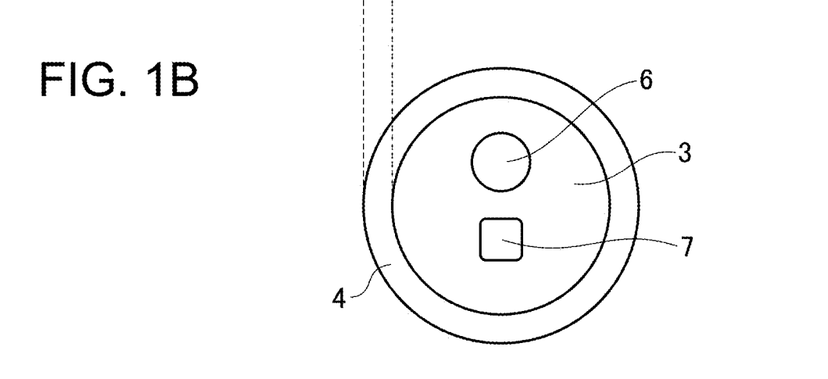
Figure 2:
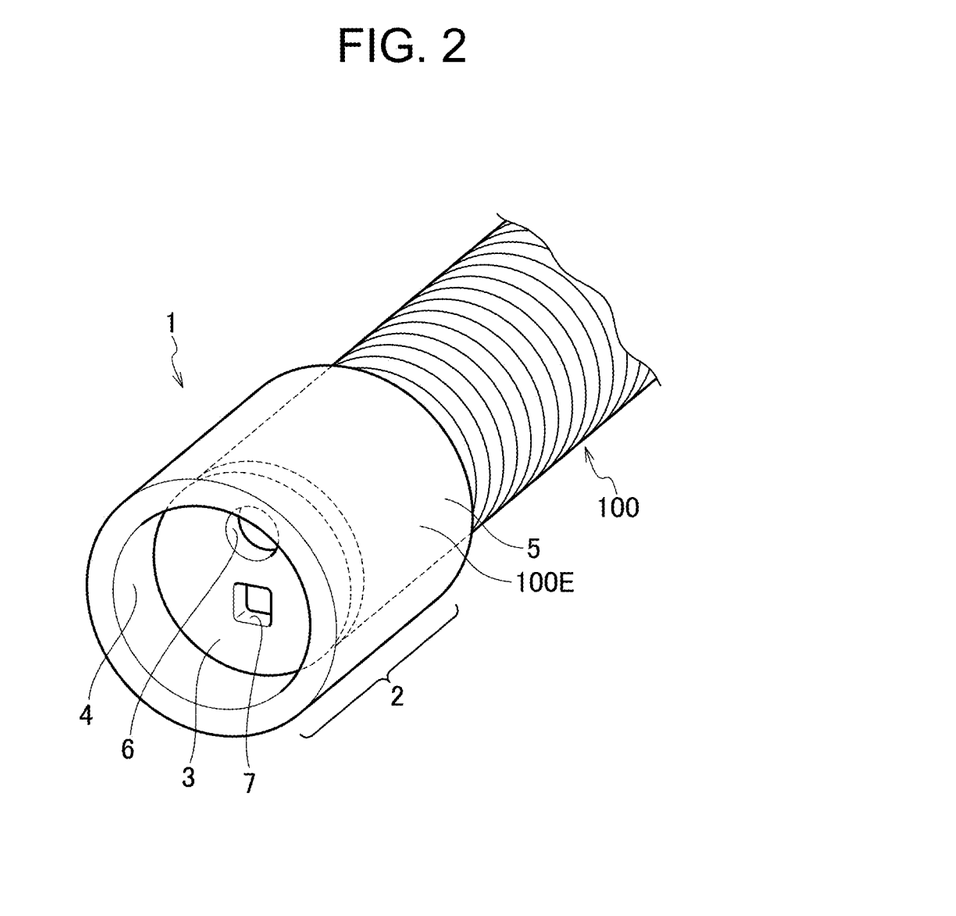
FIG. 2 is a diagram illustrating an example of a state in which the endoscope hood 1 according to the first embodiment is attached to an endoscope 100.

As illustrated in FIGS. 1A and 1B and 2, the endoscope hood 1 according to the present embodiment includes an exterior portion 2 and a disc portion 3. Here, as illustrated in FIG. 2, the endoscope hood 1 is configured to be attached to an insertion side end (tip end) 100E of the endoscope 100.

The exterior portion 2 serves as a main body of the endoscope hood 1 and has a substantially cylindrical shape. The inner surface of the exterior portion 2 is in contact with the outer surface of the endoscope 100 and is configured to fix the endoscope hood 1 to the endoscope.

As illustrated in FIGS. 1A and 1B, the exterior portion 2 serves the disc portion 3 as a boundary, and is divided into a tip end 4 for securing an optimal distance to a living tissue and a visual field, and a mounting portion 5 for fixing the endoscope hood 1 to the endoscope 100. An inner diameter f of the exterior portion 2 can be appropriately designed according to the endoscope 100 to be used.

The length a of the tip end 4 is not particularly limited as long as it is a length that can secure the optimal distance and the visual field, and the length a of the tip end 4 is preferably 1 mm to 10 mm, and more preferably 2 mm to 5 mm. If the length exceeds 10 mm, the imaging of the tip end 4 on a camera lens becomes large and the visual field narrows, which is not preferable.

In addition, when the endoscope 100 is inserted into the back portion, the tip end 4 also has a function of pushing the living tissue. Therefore, flexibility and strength are required to such an extent that the living tissue is not damaged, and thus the thickness c of the tip end 4 is preferably 0.1 mm to 1.0 mm, and more preferably 0.3 mm to 0.5 mm.

The length b of the mounting portion 5 is not particularly limited as long as it is a length sufficient to fix the endoscope hood 1 to the endoscope 100, and the length b of the mounting portion 5 is preferably 5 mm to 20 mm, and more particularly 10 mm to 15 mm. In addition, the thickness d of the mounting portion 5 is preferably 0.1 mm to 1.0 mm, and more preferably 0.3 mm to 0.5 mm.

The disc portion 3 has a disc shape and is provided in circumferential contact with the inner surface of the exterior portion 2. The disc portion 3 is formed in a substantially flat surface, and the thickness e of the disc portion 3 is preferably 0.01 mm to 1.0 mm, more preferably 0.05 mm to 0.7 mm, and most preferably 0.1 mm to 0.5 mm. When the thickness e of the disc portion 3 exceeds 1.0 mm, the visual field obtained through the camera lens is adversely affected. When the thickness e of the disc portion 3 is less than 0.01 mm, the strength of the disc portion 3 is lowered, which is not preferable because it is feared that damage occurs during use.

The disc portion 3 includes a forceps port 6 serving as an entrance and exit of a forceps, and a water supply port 7 serving as an outlet of a water supply portion for cleaning the disc portion, and the disc portion 3 is configured to be in contact with the inner surface in the middle of the exterior portion 2 and to be used by being mounted on the insertion side end 100E of the endoscope 100.

In addition, as illustrated in FIGS. 1A and 1B and 2, in the endoscope hood 1 according to the present embodiment, the exterior portion 2 and the disc portion 3 are integrally formed. In such a case, the exterior portion 2 and the disc portion 3 may be made of the same material.

In addition, the endoscope hood 1 according to the present embodiment is made of a hydrogel. Examples of the hydrogel include a hydrogel formed by using only a hydrophilic monomer, a hydrogel formed by adding a hydrophobic monomer, a crosslinkable monomer, or both to a hydrophilic monomer, and the like.

The hydrophilic monomer contributes to the moisture content of the hydrogel, and the hydrophobic monomer contributes to the adjustment action of the moisture content or the swelling ratio of the hydrogel, thereby affecting the wettability or flexibility of the obtained endoscope hood 1.

In addition, the crosslinkable monomer can control the density of the polymer chain of the hydrogel according to the content thereof, and can impart mechanical strength, shape stability, or solvent resistance to the hydrogel.

The moisture content of the hydrogel (moisture content (wt %)=[(W−D)/W]×100 (W: wet weight, D: dry weight)) is not particularly limited as long as it is moldable, and is, for example, 20 wt % to 70 wt %. In addition, if necessary, the moisture content can be appropriately selected.

For example, each of the moisture content of the exterior portion 2 and the moisture content of the disc portion 3 may be 20 wt % to 70 wt %.

As the hydrophilic monomer, a material having one or more hydrophilic groups in the molecule is preferable. Examples of the hydrophilic monomer include 2-hydroxyethyl(meth)acrylate, 2-hydroxymethyl(meth)acrylate, hydroxypropyl(meth)acrylate, glycerol(meth)acrylate, acrylamide, N,N-dimethylacrylamide, N,N-diethyl(meth)acrylamide, N-vinyl pyrrolidone, diacetone acrylamide, N-vinylacetamide, (meth)acrylic acid, (meth)acryloxyethyl succinic acid, itaconic acid, methacrylamide propyl triammonium chloride, and 2,3-dihydroxypropyl(meth)acrylate. Two or more kinds of the hydrophilic monomers may be used in combination.

Among the above-mentioned hydrophilic monomers, 2-hydroxyethyl(meth)acrylate, N,N-dimethylacrylamide, and N-vinyl pyrrolidone are preferably used from the viewpoint of handleability.

Although the blending ratio of the hydrophilic monomer is not particularly limited, the blending ratio is preferably 50 wt % or more in the entire polymerization component because it affects the moisture content of the obtained endoscope hood 1. When the blending ratio of the hydrophilic monomer is less than 50 wt %, the endoscope hood 1 having a sufficient moisture content cannot be obtained, and it is not preferable because the antifouling properties and the antifogging properties of the endoscope hood 1 may deteriorate.

Examples of the hydrophobic monomer include siloxanyl (meth)acrylate, trifluoroethyl(meth)acrylate, methacrylamide, cyclohexyl(meth)acrylate, and normal butyl(meth)acrylate. Two or more kinds of the hydrophobic monomers may be used in combination.

The hydrophobic monomer can change the hydrous property of the endoscope hood 1 obtained according to the blending amount. However, when the blending ratio of the hydrophobic monomer is high, the hydrous property is extremely lowered and the flexibility of the obtained endoscope hood 1 is lowered. Therefore, the blending ratio is preferably, for example, less than 30 wt % with respect to the total amount of the monomer.

Examples of the crosslinkable monomer include ethylene glycol di(meth)acrylate, methylene bisacrylamide, 2-hydroxy-1,3-dimethacryloxypropane, and trimethylolpropane triacrylate. Two or more of these crosslinkable monomers may be used in combination.

The blending amount of the crosslinkable monomer is preferably 0.1 wt % to 10 wt % with respect to the total amount of the monomer from the viewpoint of the shape adjustment effect of the obtained endoscope hood 1. When the blending amount of the crosslinkable monomer is less than 0.1 wt %, the network structure of the endoscope hood 1 is insufficient, and when the blending amount of the crosslinkable monomer exceeds 10 wt %, the network structure becomes excessive, the endoscope hood 1 becomes fragile, and the flexibility deteriorates.

Examples of a polymerization initiator used for polymerizing the above-mentioned mixtures of the monomers include peroxide such as lauroyl peroxide, cumene hydroperoxide, or benzoyl peroxide, which is a general radical polymerization initiator, azobisvaleronitrile, and azobisisobutyronitrile. The addition amount of the polymerization initiator is preferably about 10 ppm to about 3,500 ppm with respect to the total amount of the monomer.

The endoscope hood 1 according to the present embodiment is one which forms a desired shape after mixing one or more of the above-mentioned monomers and is made of a single material.

As the process of obtaining the polymer, a monomer mixed solution obtained by mixing monomers as constituent components is placed in a metal, glass, or plastic mold and airtightly sealed, a temperature is raised stepwise or continuously in a thermostat or the like in the range of 25° C. to 120° C., and a copolymerization reaction is completed for 5 hours to 120 hours, thereby obtaining a polymer-containing mold. With regard to the polymerization, ultraviolet rays, electron beams, gamma rays, and the like can be used.

As the process of obtaining the hydrogel, the mold after the completion of the polymerization is cooled to room temperature, the polymer contained in the mold is released from the mold, and if necessary, after cutting and polishing, the polymer is hydrated and swollen to obtain the hydrogel. Examples of the liquid (swelling liquid) to be used include water, physiological saline, isotonic buffer, and a solution prepared by mixing an organic solvent such as ethanol, but are not limited thereto. The swelling liquid is heated to 60° C. to 100° C., and the polymer is immersed in the swelling liquid for a certain time, thereby making a swollen state. In addition, it is also preferable to remove unreacted monomers attached to the polymer during the swelling treatment. The obtained hydrogel can be shaped by subjecting the hydrogel to high pressure steam sterilization at 110° C. to 130° C. for 10 minutes to 60 minutes in a state of being immersed in a swelling liquid such as a physiological saline solution.

The endoscope hood 1 according to the present embodiment is excellent in the antifogging properties and the antifouling properties. Therefore, at the time of the surgery or examination, body fluid or fat and oil attached to the lens part can be easily removed by water sprayed from the water supply mechanism provided in the endoscope 100. Furthermore, fogging can be suppressed. Therefore, in the surgery or examination over a long period of time, it is unnecessary to take out the endoscope 100 so as to remove contamination or fogging of the lens part. Therefore, it is possible to shorten the surgery or examination and reduce the burden on the patient.

Hereinafter, an endoscope hood 1 according to a further embodiment will be described with reference to FIGS. 3A and 3B, focusing on differences from the above-described endoscope hood 1 according to the first embodiment.

Figure 3A:
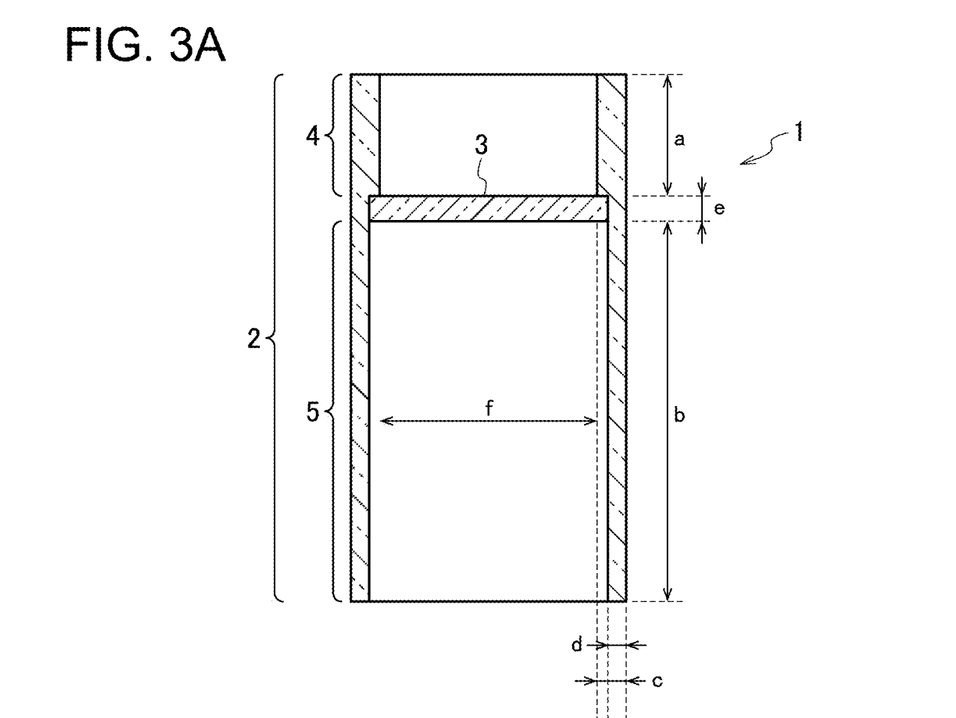
FIG. 3A is an example of a cross-sectional view and FIG. 3B is a plan view of an endoscope hood 1 according to a second embodiment.
Figure 3B:
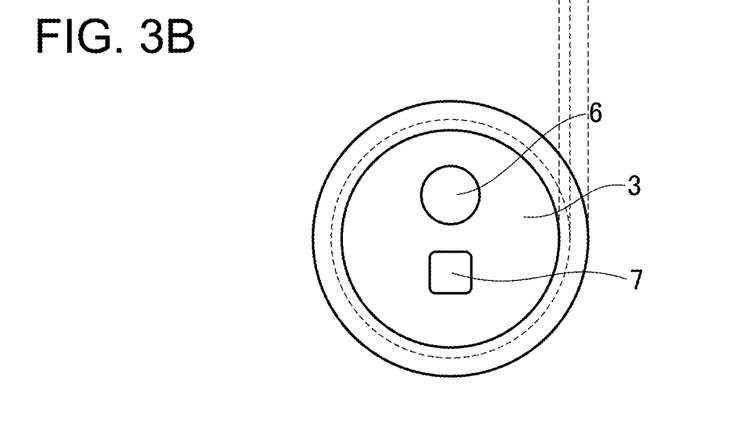

In the endoscope hood 1 according to the present embodiment, as illustrated in FIGS. 3A and 3B, an exterior portion 2 and a disc portion 3 are separately molded. The exterior portion 2 and the disc portion 3 are configured to be attached to an insertion side end (tip end) 100E of an assembled endoscope 100.

Here, in the endoscope hood 1 according to the present embodiment, the exterior portion 2 and the disc portion 3 may be made of different materials.

In such a case, the moisture content of the exterior portion 2 is 20 wt % to 70 wt %, and the moisture content of the disc portion 3 may be greater than the moisture content of the exterior portion 2. According to such a configuration, the antifogging properties and the antifouling properties can be more effectively exhibited.

In addition, in the endoscope hood 1 according to the present embodiment, from the viewpoint of pressability for fixing the disc portion 3 to the insertion side end 100E of the endoscope 100 and fixability of the endoscope hood 1, it is preferably formed in the range of 50% to 95% with respect to the thickness c of the tip end 4.

As described above, the present invention has been described with reference to the above-described embodiments, but it should not be understood that the description and drawings constituting a part of the disclosure in such embodiments limit the present invention. From this disclosure, various alternative embodiments, examples, and operational technologies will become apparent to those skilled in the art.

EXAMPLE

Hereinafter, examples of the present invention will be described in more detail with reference to FIGS. 4 to 8, but the present invention is not limited to these examples.

(Production of Endoscope Hood 1 According to Example 1)

99 g of 2-hydroxyethyl methacrylate as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the endoscope hood 1 shown in Table 1 (temperature increase from room temperature to 100° C. in a nitrogen atmosphere for 40 hours). The obtained copolymer before swelling was swollen by heating in physiological saline at 60° C. for 30 minutes and subjected to high pressure steam sterilization to thereby produce the endoscope hood 1 according to Example 1.

(Production of Endoscope Hood 1 According to Example 2)

99 g of N-vinylpyrrolidone as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the endoscope hood 1 shown in Table 1 (temperature increase from room temperature to 100° C. in a nitrogen atmosphere for 40 hours). The obtained copolymer before swelling was swollen by heating in physiological saline at 60° C. for 30 minutes and subjected to high pressure steam sterilization to thereby produce the endoscope hood 1 according to Example 2.

(Production of Endoscope Hood 1 According to Example 3)

First, 99 g of 2-hydroxyethyl methacrylate as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the exterior portion 2 shown in Table 1 (temperature increase from room temperature to 10° C. in a nitrogen atmosphere for 40 hours).

Next, 64 g of N,N-dimethylacrylamide and 35 g of 2-hydroxyethyl methacrylate as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the disc portion 3 shown in Table 1 (temperature increase from room temperature to 100° C. in a nitrogen atmosphere for 40 hours). The obtained copolymers of the shape of the exterior portion 2 and the shape of the disc portion 3 before swelling were swollen by heating in physiological saline at 60° C. for 30 minutes and subjected to high pressure steam sterilization to thereby produce the endoscope hood 1 according to Example 3.

(Production of Endoscope Hood 1 According to Example 4)

First, 99 g of 2-hydroxyethyl methacrylate as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the exterior portion 2 shown in Table 1 (temperature increase from room temperature to 100° C. in a nitrogen atmosphere for 40 hours).

Next, 60 g of N-vinylpyrrolidone and 36 g of 2-hydroxyethyl methacrylate as the hydrophilic monomer, 1 g of ethylene glycol dimethacrylate as the crosslinkable monomer, and 0.15 g of 2,2'-azobisisobutyronitrile as the polymerization initiator were mixed, and after swelling, heat polymerization was performed in a mold designed beforehand so as to have the structure of the disc portion 3 shown in Table 1 (temperature increase from room temperature to 100° C. in a nitrogen atmosphere for 40 hours). The obtained copolymers of the shape of the exterior portion 2 and the shape of the disc portion 3 before swelling were swollen by heating in physiological saline at 60° C. for 30 minutes and subjected to high pressure steam sterilization to thereby produce the endoscope hood 1 according to Example 4.

Evaluation of Antifogging Properties and Antifouling Properties

Examples 1 to 4 and Comparative Example 1

For Examples 1 to 4, the endoscope hood 1 according to Examples 1 to 4 formed as described above was attached to the insertion side end 100E of the commercially available endoscope 100. For Comparative Example 1, the commercially available endoscope hood coated with the commercially available antifogging material was applied to the disc portion 3. The commercially available endoscope hood according to Comparative Example 1 is "Elastic Touch" manufactured by Top Co., Ltd., and is made of polyvinyl chloride. In addition, the commercially available anti-fogging material according to Comparative Example 1 is "Cleash" manufactured by Nagase Medicals Co., Ltd. and is composed of a nonionic surfactant.

Next, lard was applied to the disc portions 3 of Examples 1 to 4 and Comparative Example 1 by using a cotton swab, water of room temperature was sprayed from the water supply mechanism for 10 seconds, and the antifogging properties and the antifouling properties were evaluated according to the following conditions.

Figure 4A:
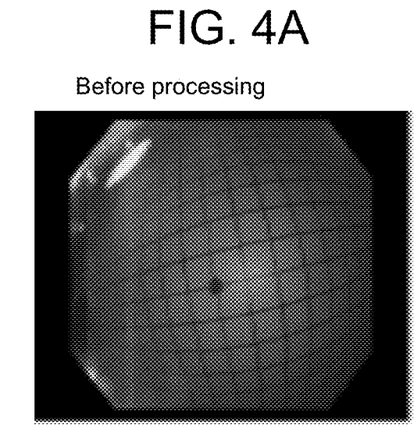
FIG. 4A, FIG. 4B and FIG. 4C are diagrams for describing an example.
Figure 4B:
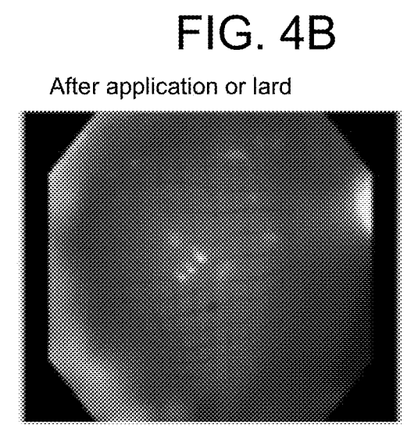
Figure 4C:
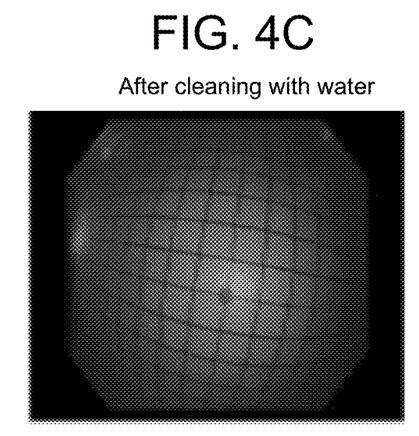

FIG. 4A illustrates a state before the application of the lard in the disc portion 3 of the endoscope hood 1 according to Example 1, FIG. 4B illustrates a state after the application of the lard in the disc portion 3 of the endoscope hood 1 according to Example 1, and FIG. 4C illustrates a state after cleaning with the water sprayed in the disc portion 3 of the endoscope hood 1 according to Example 1.

Figure 5A:
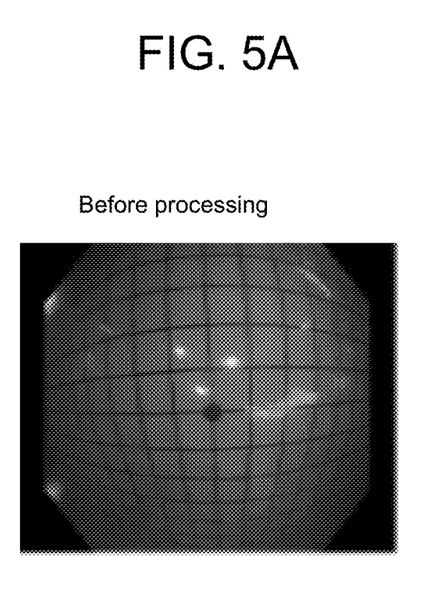
FIG. 5A, FIG. 5B and FIG. 5C are diagrams for describing an example.
Figure 5B:
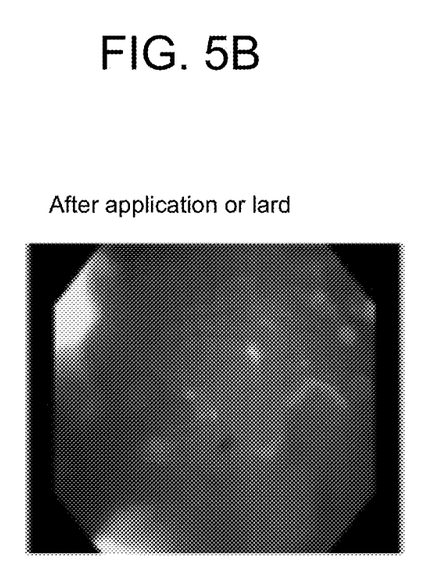
Figure 5C:
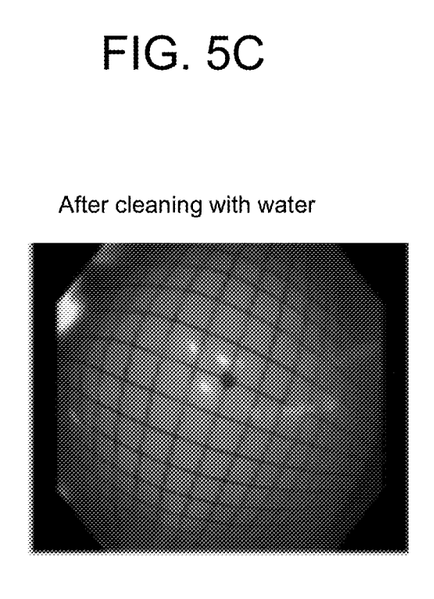

FIG. 5A illustrates a state before the application of the lard in the disc portion 3 of the endoscope hood 1 according to Example 2, FIG. 5B illustrates a state after the application of the lard in the disc portion 3 of the endoscope hood 1 according to Example 2, and FIG. 5C illustrates a state after cleaning with the water sprayed in the disc portion 3 of the endoscope hood 1 according to Example 2.

Figure 6A:
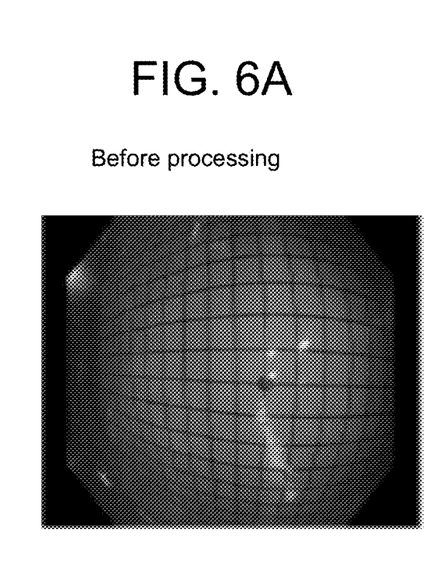
FIG. 6A, FIG. 6B and FIG. 6C are diagrams for describing an example.
Figure 6B:
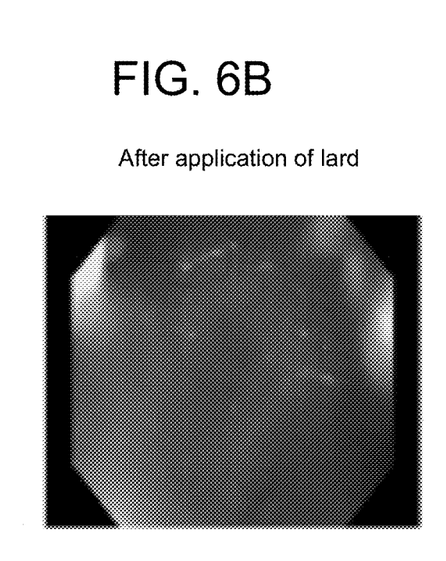
Figure 6C:
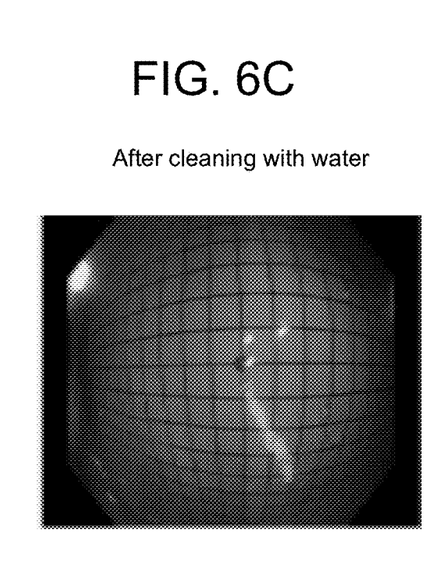

FIG. 6A illustrates a state before the application of the lard in the disc portion 3 of the endoscope hood 1 according to Example 3, FIG. 6B illustrates a state after the application of the lard in the disc portion 3 of the endoscope hood 1 according to Example 3, and FIG. 6C illustrates a state after cleaning with the water sprayed in the disc portion 3 of the endoscope hood 1 according to Example 3.

Figure 7A:
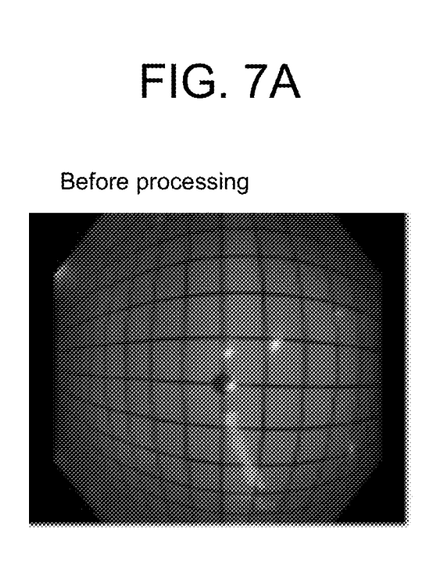
FIG. 7A, FIG. 7B and FIG. 7C are diagrams for describing an example.
Figure 7B:
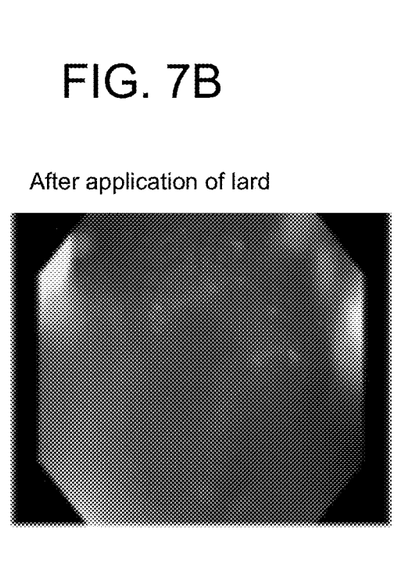
Figure 7C:
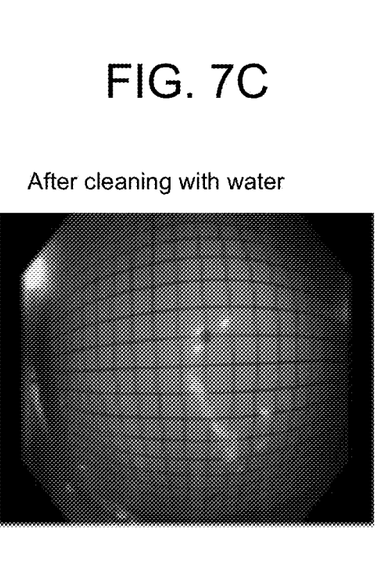

FIG. 7A illustrates a state before the application of the lard in the disc portion 3 of the endoscope hood 1 according to Example 4, FIG. 7B illustrates a state after the application of the lard in the disc portion 3 of the endoscope hood 1 according to Example 4, and FIG. 7C illustrates a state after cleaning with the water sprayed in the disc portion 3 of the endoscope hood 1 according to Example 4.

Figure 8A:
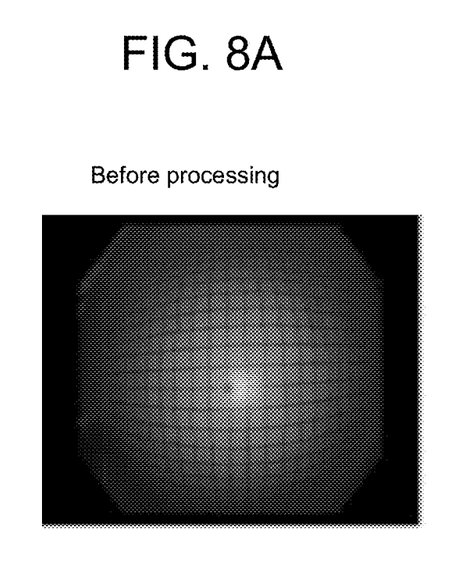
FIG. 8A, FIG. 8B and FIG. 8C are diagrams for describing an example.
Figures 8B, 8C:
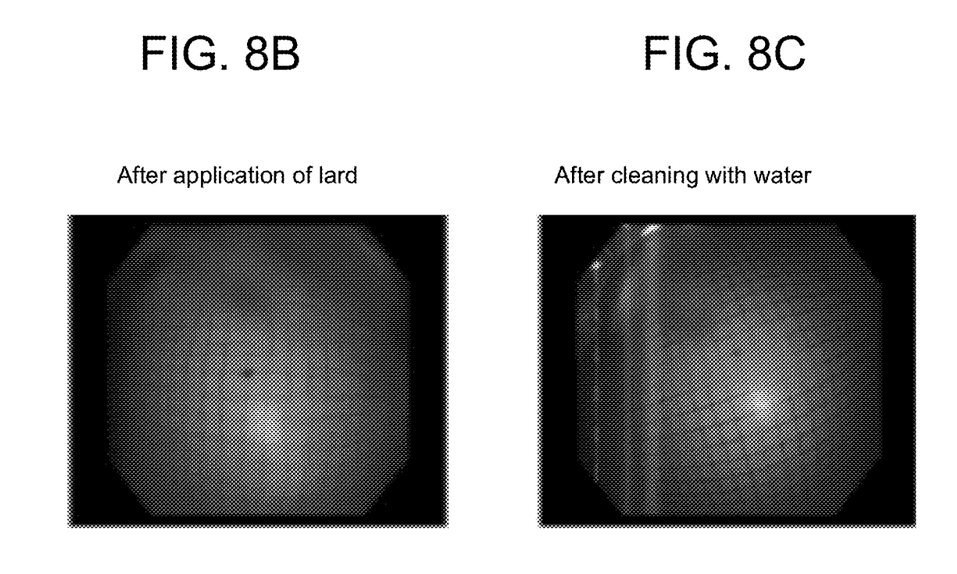

FIG. 8A illustrates a state before the application of the lard in the disc portion 3 of the endoscope hood 1 according to Comparative Example 1, FIG. 8B illustrates a state after the application of the lard in the disc portion 3 of the endoscope hood 1 according to Comparative Example 1, and FIG. 8C illustrates a state after cleaning with the water sprayed in the disc portion 3 of the endoscope hood 1 according to Comparative Example 1. "⊚", "○", and "x", which are the symbols shown in Table 1, indicate the following evaluation results.

⊚: No lard is attached to the lens part.

○: The attachment of the lard to the lens part is observed, but it does not interfere with visibility.

x: The lard is attached to the lens part, and the visibility is poor.

The evaluation results of the anti-fogging properties and the antifouling properties are shown in the following Table 1.

TABLE 1

|  |  | Example 1 | Example 2 | Example 3 | Example 4 | Comparative Example 1 |
|---|---|---|---|---|---|---|
| Moisture content (%) of exterior portion | | 38.0 | 67.0 | 38.0 | 38.0 | — |
| Moisture content (%) of disc portion | | | | 60.0 | 67.0 | — |
| Tip end | Length (mm) | 14.0 | 14.0 | 4.0 | 4.0 | 13.0 |
|  | Thickness (mm) | 1.0 | 1.0 | 1.0 | 1.0 | 1.3 |
| Mounting portion | Length (mm) | 14.0 | 14.0 | 14.0 | 14.0 | 3.3 |
|  | Thickness (mm) | 1.0 | 1.0 | 1.0 | 1.0 | 0.6 |
| Disc portion | Thickness (mm) | 0.5 | 0.5 | 0.5 | 0.5 | — |
| Evaluation results of antifogging and antifouling properties | | ○ | ⊚ | ⊚ | ⊚ | X |

According to the above-described aspects, it is possible to provide an endoscope hood having excellent antifogging properties and antifouling properties.

The invention claimed is:

1. An endoscope hood to be mounted on an insertion side end of an endoscope, the endoscope hood comprising:
   a cylindrical portion comprising an inner surface and an exterior portion; and
   a disc portion provided in contact with the inner surface of the cylindrical portion, wherein a thickness of the disc portion is 0.4 mm to 0.5 mm, and a thickness of the exterior portion is 0.5 mm to 1.0 mm, wherein:
- the exterior portion and the disc portion are formed separately,
- the exterior portion and the disc portion are made of hydrogels, wherein the hydrogel forming the exterior portion has a moisture content of 20 wt % to 70 wt %, and the hydrogel forming the disc portion has a moisture content greater than the moisture content of the exterior portion; and
- each hydrogel comprises a polymer formed by ethylene glycol dimethacrylate and a hydrophilic monomer selected from the group consisting of: 2-hydroxyethyl methacrylate, N-vinylpyrrolidone, and N—N-dimethylacrylamide.

2. The endoscope hood according to claim 1, wherein the exterior portion and the disc portion are made of the same material.

3. The endoscope hood according to claim 1, the exterior portion and the disc portion are made of different materials from each other.

4. The endoscope hood according to claim 1, wherein the moisture content of the exterior portion is 20 wt % to 50 wt % and the moisture content of the disc portion is greater than 50 wt %.

\* \* \* \* \*